United States Patent [19]

Ryan

[11] Patent Number: 5,262,327
[45] Date of Patent: Nov. 16, 1993

[54] WHITE BLOOD CELL HEMATOLOGY CONTROL

[75] Inventor: Wayne L. Ryan, Omaha, Nebr.

[73] Assignee: Streck Laboratories, Inc., Omaha, Nebr.

[21] Appl. No.: 66,912

[22] Filed: May 24, 1993

Related U.S. Application Data

[63] Continuation of Ser. No. 697,331, May 9, 1991, abandoned.

[51] Int. Cl.$^5$ ............................................. G01N 33/49
[52] U.S. Cl. ...................................... 436/10; 436/16; 436/8; 424/3
[58] Field of Search ................... 436/8, 10, 13, 15–18; 435/2; 424/3

[56] References Cited

U.S. PATENT DOCUMENTS

| | | | |
|---|---|---|---|
| 3,558,522 | 1/1971 | Louderback | 436/18 X |
| 4,099,917 | 7/1978 | Kim | 436/10 |
| 4,160,644 | 7/1979 | Ryan | 436/10 |
| 4,219,440 | 8/1980 | Runck et al. | 436/10 |
| 4,264,470 | 4/1981 | Chastain, Jr. et al. | 436/10 |
| 4,324,687 | 4/1982 | Louderback et al. | 436/10 |
| 4,358,394 | 11/1982 | Crews et al. | 436/10 |
| 4,389,490 | 6/1983 | Crews et al. | 436/10 X |
| 4,436,821 | 3/1984 | Ryan | 436/11 X |
| 4,698,312 | 10/1987 | Wong et al. | 436/10 |
| 4,704,364 | 11/1987 | Carver et al. | 436/10 |
| 4,745,071 | 5/1988 | Lapicola et al. | 436/17 X |
| 4,777,139 | 10/1988 | Wong et al. | 436/17 X |

OTHER PUBLICATIONS

Lombarts, et al. "A White Blood Cell Control of Long-term Stability" Clinica Chimica Acta, vol. 129, pp. 79–83 (1983).

Lombarts, et al. "A Stable Human Platelet-White Blood Cell Control for the Coulter Model S-Plus II" Clinica Chimica Acta, vol. 130, pp. 95–102 (1983).

*Primary Examiner*—James C. Housel
*Assistant Examiner*—Jeffrey R. Snay
*Attorney, Agent, or Firm*—Tilton, Fallon, Lungmus & Chestnut

[57] ABSTRACT

Reference controls comprised of aldehyde-fixed white blood cells exhibiting a white blood cell histogram profile that is substantially that of whole blood are obtained by the additions of a lipoprotein to the control.

10 Claims, 6 Drawing Sheets

WHITE BLOOD CELL HEMATOLOGY CONTROL

This application is a continuation, of application Ser. No. 07/697,331 filed May 9, 1991, now abandoned.

BACKGROUND OF INVENTION

1. Field of the Invention

The present invention relates to a method for preparing a hematology reference control and calibrator for hematology instruments used to measure granulocytes, lymphocytes, monocytes, eosinophiles and basophiles.

2. Prior Art

There are several hematology instruments which can analyze blood to determine the number of granulocytes, monocytes, lymphocytes, eosinophiles and basophiles. These instruments include the Coulter STKS, Unipath 3000, TOA NE 8000, Technicon H-1 and Technicon H-6000. Because these instruments employ different methods to measure the five populations of white cells, it has been necessary to employ a different type of reference control with each instrument. This fact has necessitated that the manufacturer stocks separate controls for each of the types of instruments they supply. From the manufacturers' standpoint, this situation is not only inconvenient, but can be expensive as well.

SUMMARY OF THE INVENTION

It is an object of the present invention to provide a reference control that can be used in a variety of hematology instruments.

It is a further object of the invention to provide a reference control that can be used for proficiency testing. Currently, when unknown samples are sent to laboratories to measure the proficiency of the laboratory to assay them, multiple samples are required. Because, the control of the present invention is operative on all available instruments makes, it is possible to use a single control for testing all of the differential instruments.

The present invention provides a reference control for hematology instruments comprising:

i) white blood cells fixed with an aldehyde fixing agent suspended in an isotonic aqueous suspension medium; and ii) a composition comprising at least one lipoprotein in an amount sufficient to provide a mixture that gives a white blood cell histogram profile that is substantially the same as that of whole blood.

In a preferred embodiment, the aldehyde fixative comprises a mixture of formaldehyde and glutaraldehyde in a ratio of 3 to 15 ml formaldehyde: 0.01 to 1 ml of glutaraldehyde per 100 ml of fixing solution. As will be discussed below, the uses of a mixture of formaldehyde and a small amount of glutaraldehyde reduces the amount of lipoprotein necessary to provide a histogram profile for fixed or stabilized white blood cell controls that is substantially the same as that of blood. Particularly preferred reference controls of the invention further include predetermined amounts of both stabilized red blood cells and simulated blood platelets.

The invention also provides a method of preparing a stabilized reference control for hematology instruments comprising mixing white blood cells fixed with an aldehyde fixing agent, an isotonic aqueous suspension medium and at least one lipoprotein in an amount sufficient to provide a mixture that gives a white blood cell histogram profile that is substantially the same as that of blood.

DETAILED DESCRIPTION OF THE INVENTION

When fresh whole blood samples are collected, they contain five different white cell subpopulations, four of which can be seen in the histograms in FIGS. 1A, 1B and 1C and FIGS. 2A, 2B and 2C obtained using a Coulter STKS. The four visible populations are monocytes 10, neutrophiles 12, eosinophiles 14 and lymphocytes 16.

When these subpopulations of white blood cells are separated from whole blood as, for instance, by differential centrifugation, washed with isotonic saline and used to prepare a reference control, the histogram of the resulting control is different in appearance from that of whole blood. In fact, the more the white blood cells are washed the more the histogram changes. A change in a white blood cell histogram due to washing is shown in FIG. 2. From these experiments it is clear that something responsible for the proper positioning in the histogram of white cell subpopulations is being removed. Similarly, when histograms are taken of reference controls made up of white blood cells washed and fixed with aldehyde fixing agents, the result is again an improper positioning of the white blood cell subpopulations.

It has been unexpectedly found that the addition of an effective amount of a composition comprising at least one lipoprotein to an aqueous isotonic suspension of aldehyde fixed white blood gives a white blood histogram profile that is substantially that of whole blood. The finding was particularly surprising since other proteins have little effect on the positioning of the white blood cell populations. For example, reference samples containing commercially available proteins such as albumin, alpha-globulin, beta-globulin, gamma-globulin and fibrinogen were tested in the STKS and found to have an insignificant effect on the positioning.

Figure 1A:
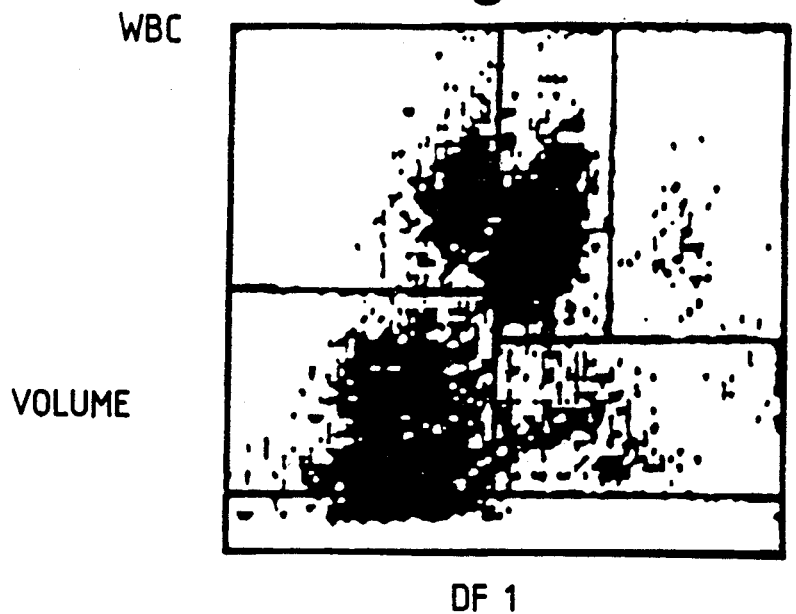
FIGS. 1A, 1B and 1C illustrate a portion of a white blood cell histogram for whole blood made using a Coulter STKS.
Figure 1B:
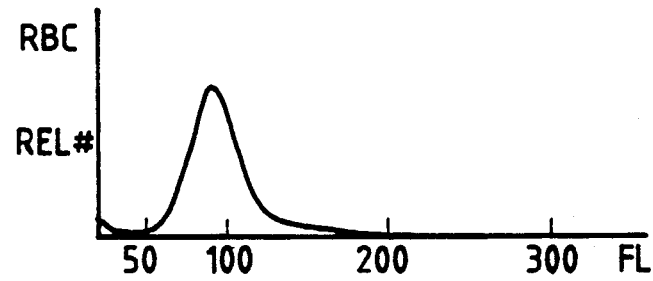
Figure 1C:
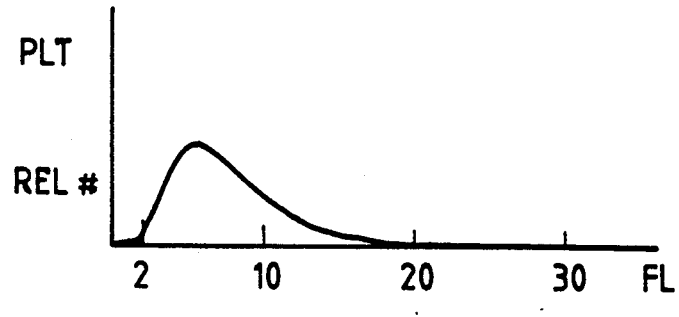
Figure 2A:
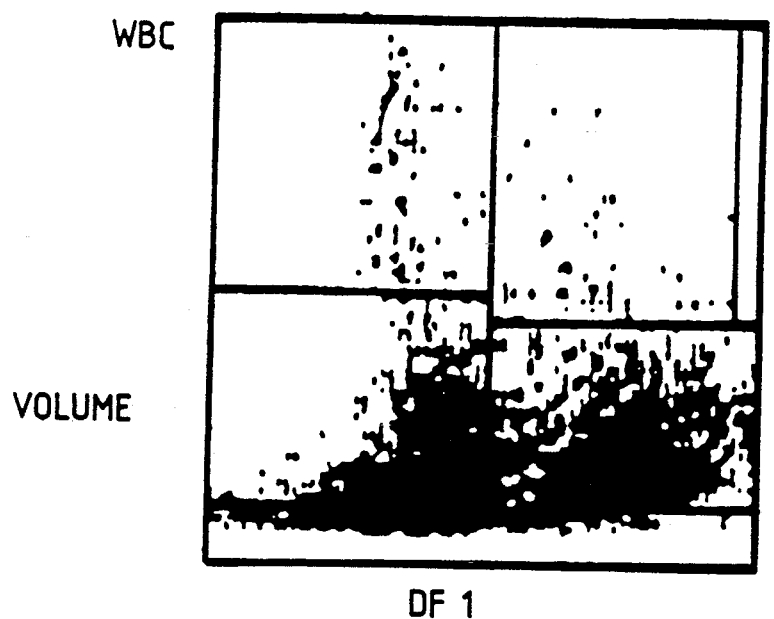
FIGS. 2A, 2B and 2C are a white blood cell histogram made after washing the white blood cells in FIGS. 1A, 1B and 1C with an isotonic saline solution.
Figure 2B:
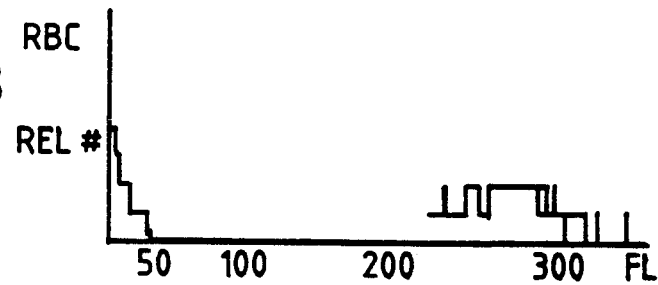
Figure 2C:
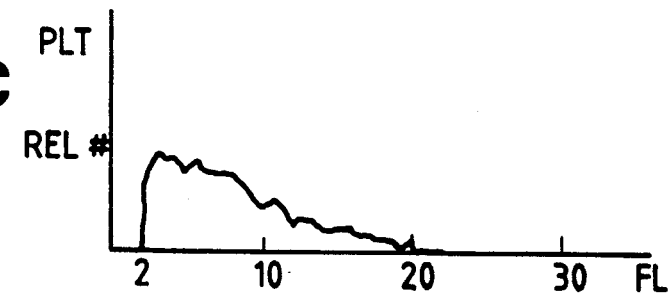
Figure 3A:
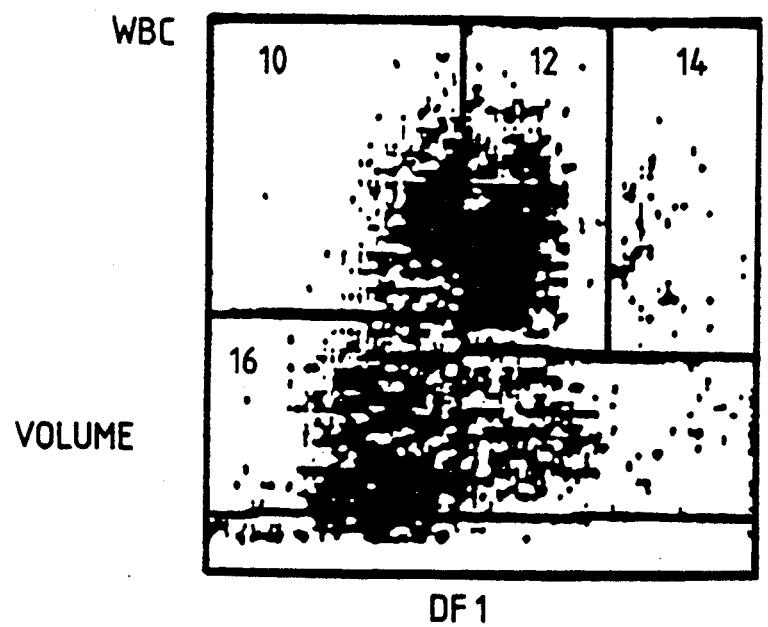
FIGS. 3A, 3B and 3C are a white blood cell histogram made after treating the white blood cells in FIGS. 2A, 2B and 2C with concentrated serum.
Figure 3B:
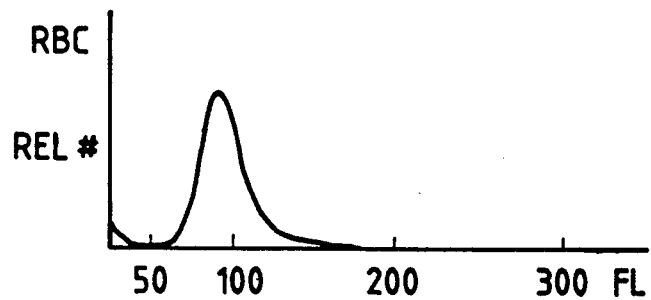
Figure 3C:
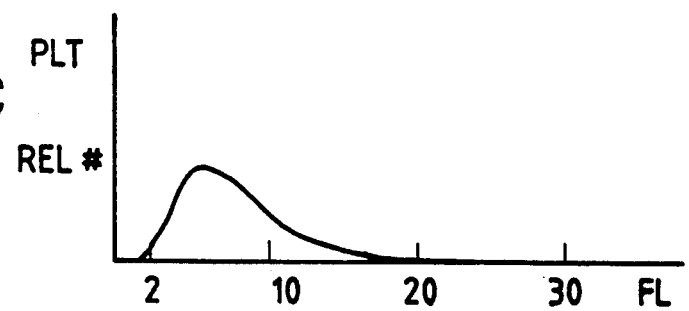
Figure 4A:
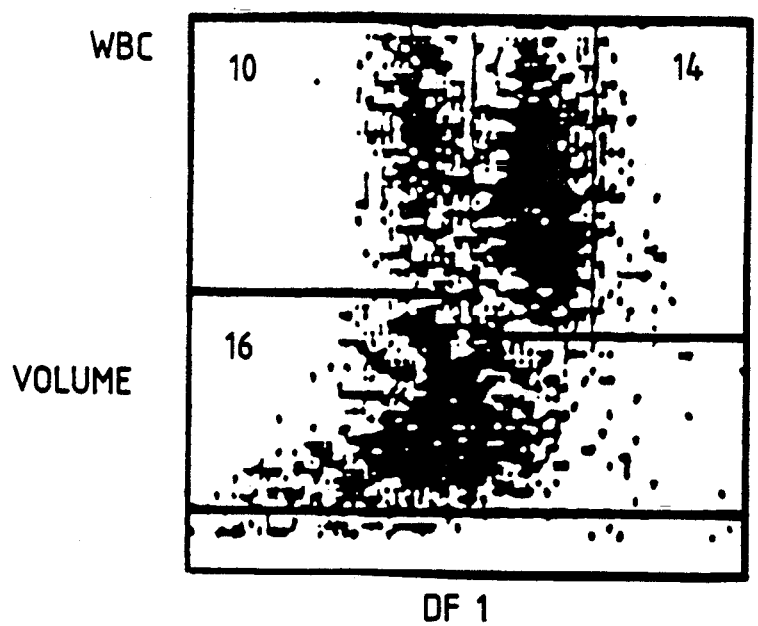
FIGS. 4A, 4B and 4C are a white blood cell histogram made after treating the fixed white blood cells with a concentrated plasma solution.
Figure 4B:
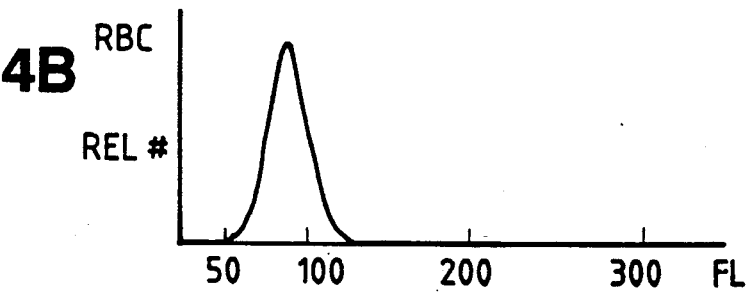
Figure 4C:
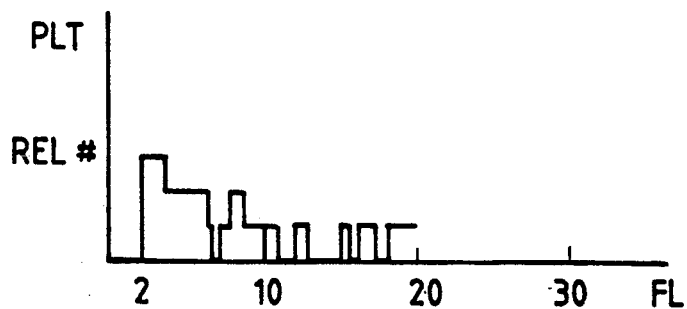
Figure 5A:
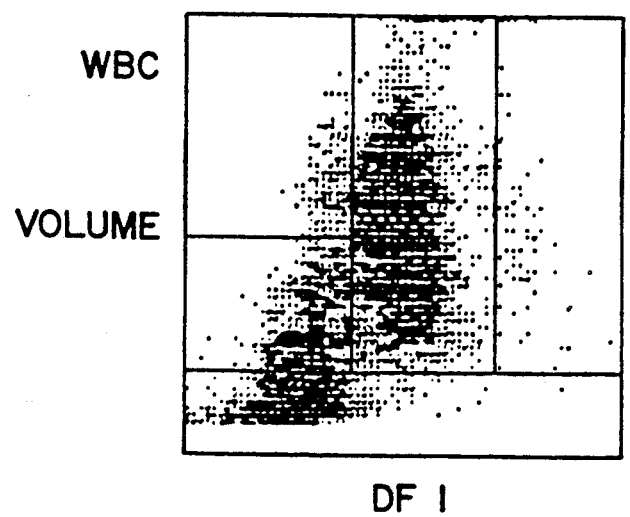
FIGS. 5A, 5B and 5C are a white blood cell histogram made before treating fixed white blood cells with a high density lipoprotein.
Figure 5B:
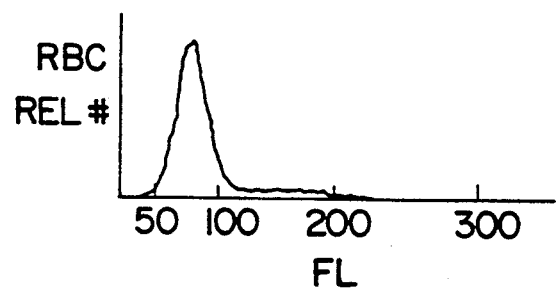
Figure 5C:
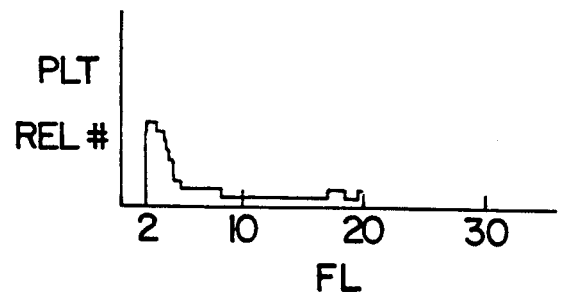

The lipoproteins suitable for use in the present invention can be either high or low density lipoproteins, both of which are available from a number of commercial sources. Lipoproteins from the serum of various animals, (e.g. horse and bovine) and egg yolk lipoprotein all have been found to exhibit the desired effect. (See FIGS. 5A, 5B, and 5C) It is also possible to use compositions containing lipoproteins as the lipoprotein source.

Examples of such lipoprotein sources are animal (include man) blood serums and plasmas. (See FIGS. 3A, 3B and 3C and FIGS. 4A, 4B and 4C) Where such lipoprotein-containing compositions are employed, the amount of composition employed in the reference controls of the invention will depend upon the concentration of the lipoprotein. Preferred blood plasma or serum concentrates are those concentrated two to three fold so as to contain about 14 to 17% by weight of protein.

As aforementioned, the amount of lipoprotein added to the stabilized white blood cells is that which effectively moves the white blood cell subpopulations in the histogram to the correct position, i.e. so that the histogram substantially mimics the white blood cell histogram for whole blood. Generally, the amount of lipoprotein in the final product will vary from about 0.5 to 8.0% by volume, depending upon the type of lipoprotein used. For example, two to three times more low density protein is required than high density lipoproteins. When egg lipoproteins are used about 30% more is necessary than high density lipoprotein.

The aqueous suspension medium employed in the reference control of the invention is one that is non-deleterious to the white blood cells and, optionally, red blood cells or platelets to be counted. The suspension medium is preferably a physiological salt solution such as an isotonic salt solution, advantageously buffered to a pH neutral to alkaline, preferably a pH of 7 to 9. Preferred buffering agents include alkali metal phosphates such as disodium phosphate, monopotassium phosphate, monosodium phosphate, sodium citrate and the like and mixtures thereof.

The white blood cells of the reference control of the invention are fixed with an aldehyde fixing agent to partially rigidify their cell membranes and render them stable. Aldehyde fixing agents for white blood cells are well known and include, for instance, formaldehyde and glutaraldehyde. The fixatives are preferably prepared in phosphate buffered saline. The amount of aldehyde employed in the fixatives will vary depending upon the particular aldehyde employed but normally falls in the range of about 1 to 10% by volume of fixing agent. The preferred fixative is a mixture of formaldehyde and glutaraldehyde in a ratio of 0.01 to 1.0 ml of glutaraldehyde: 3 to 15 ml formaldehyde per 100 ml of fixative. It has been discovered that reference controls made up of white blood cells fixed with the mixture of formaldehyde and glutaraldehyde require less lipoprotein to properly position the white blood cells. The presence of a small amount of glutaraldehyde decreases the amount of lipoprotein.

Advantageously, the reference control of the invention may also include stabilized red blood cells and simulated blood platelets commonly employed in prior art reference controls in a number, size, and distribution equal to that of human whole blood. Suitable simulated blood platelets are described in U.S. Pat. Nos. 4,436,821 and 4,160,644.

The invention will now be further described with reference to the examples below.

EXAMPLE 1

Human white blood cells are obtained as concentrates from commercial blood banks. The white blood cells are washed and freed of red blood cells by placing in ammonium chloride-tris for several minutes. Tris-ammonium chloride buffer is prepared by adding 7.5 g of ammonium chloride and 2.0 g of Trizma base (tris (hydroxy methyl) amino methane) to one liter of distilled water. The white blood cells are stabilized by adding phosphate buffered saline containing 13 ml of 37% formaldehyde/100 ml of phosphate buffered saline. The cells are held in the fixative for 24 hours and then washed with phosphate buffered saline. The white blood cells are added to a red cell preservative diluent containing lipoprotein. The amount of lipoprotein varies with the purity and type used. The commercial preparation used is Miles Supertratex® and it is used at 0.5–5% V/V.

EXAMPLE 2

White blood cells are fixed with 37% formaldehyde diluted to 13% v/v in phosphate buffered saline containing 0.33 ml of 25% glutaraldehyde. After fixing for 24 hours the cells are washed with saline and added to red cells in a stabilizing solution containing sodium citrate, magnesium gluconate and antibiotics. After adding the white blood cells, simulated platelets prepared as described in U.S. Pat. No. 4,160,644 are added.

The simulated platelets and the white blood cells are added to the red cells in the stabilizing diluent at normal, high abnormal and low abnormal levels. Finally lipoprotein (Supertrate Miles—a high density lipoprotein >70%, protein 5.8, 48–49 dynes/cm$^2$) is added at a concentration of 2% v/v (0.5–5.0%).

Figure 6A:
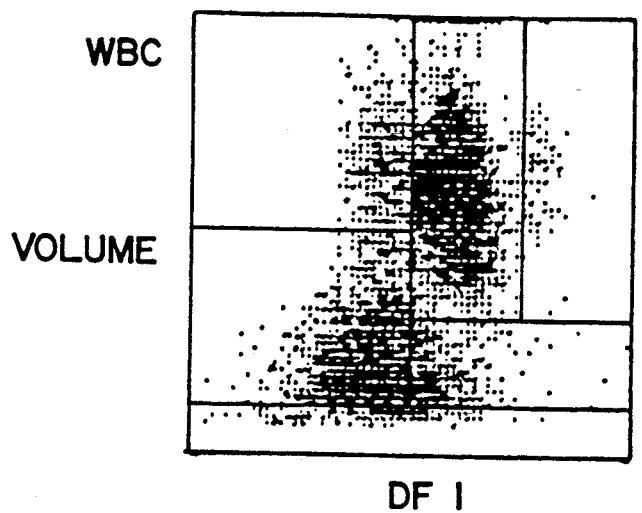
FIGS. 6A, 6B and 6C show a histogram on Coulter STKS of the completed product. This product also provides a 5-part differential on the Sysmex NE-8000, Technicon H-1, Technicon H-6000, Cell-Dyne 3000 as well as the Coulter STKS.
Figure 6B:
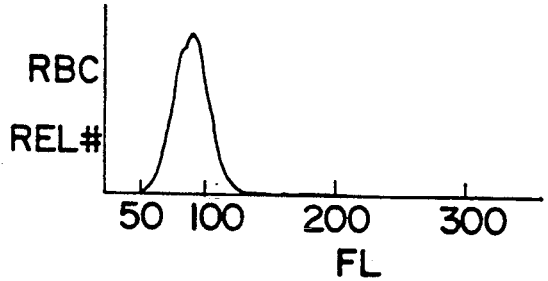
Figure 6C:
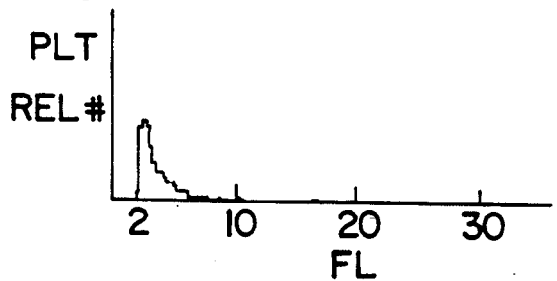

Example of final values for normal control:
red blood cells—$4.75 \times 10^6$/mm$^3$
white blood cells—$8 \times 10^3$/MM$^3$
Platelets $225 \times 10^3$/mm$^3$ FIGS. 6A, 6B and 6C show a histogram on STKS of the completed product. This product also provides a 5-part differential on the Sysmex NE-8000, Technicon H-1, Technicon H-6000, Cell-Dyne 3000 as well as the STKS.

It is claimed:

1. A reference control for hematology instruments comprising:
   i) white blood cells fixed with an aldehyde fixing agent, stabilized red blood cells and simulated blood platelets, suspended in an isotonic aqueous suspension medium; and
   ii) a composition comprising at least one lipoprotein in an amount sufficient to provide a mixture that gives a white blood cell histogram profile that is substantially that of whole blood.

2. The reference control of claim 1, wherein the suspension medium comprises buffered saline solution.

3. The reference control of claim 1, wherein the at least one lipoprotein is a high density lipoprotein.

4. The reference control of claim 1 wherein said fixative agent comprises a mixture of formaldehyde and glutaraldehyde in a ratio of 3 to 15 ml formaldehyde: 0.01 to 1 ml of glutaraldehyde per 100 ml of fixing solution.

5. The reference control of claim 1, wherein the at least one lipoprotein is added in the form of a concentrated blood serum or plasma.

6. A method for making a reference control for hematology instruments comprising mixing white blood cells fixed with an aldehyde fixing agent, stabilized red blood cells and simulated blood platelets in an isotonic aqueous suspension medium with at least one lipoprotein in an amount sufficient to provide a mixture that gives a white blood cell histogram profile that is substantially the same as that of blood.

7. The method of claim 6, wherein the suspension medium comprises buffered saline solution.

8. The method of claim 1, wherein the at least one lipoprotein is a high density lipoprotein.

9. The method of claim 6, wherein the white blood cells are fixed with a mixture of formaldehyde and glutaraldehyde in a ratio of 3 to 15 ml formaldehyde: 0.01 to 1 ml of glutaraldehyde per 100 ml of fixing solution.

10. The method of claim 9, wherein the at least one lipoprotein is added in the form of a concentrated blood serum or plasma.

* * * * *